US012533254B2

(12) United States Patent
Wenzel et al.

(10) Patent No.: US 12,533,254 B2
(45) Date of Patent: Jan. 27, 2026

(54) EXOSKELETON WITH A BACK PLATE

(71) Applicant: Drager Safety AG & Co. KGaA, Lübeck (DE)

(72) Inventors: Lennart Wenzel, Lübeck (DE); Peer Groß, Lübeck (DE); Torben Söker, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 5 days.

(21) Appl. No.: 18/611,873

(22) Filed: Mar. 21, 2024

(65) Prior Publication Data

US 2024/0315864 A1 Sep. 26, 2024

(30) Foreign Application Priority Data

Mar. 24, 2023 (DE) ..................... 10 2023 107 409.1

(51) Int. Cl.

*A61F 5/02* (2006.01)
*A61F 5/01* (2006.01)
*A61H 3/00* (2006.01)

(52) U.S. Cl.

CPC ................. *A61F 5/02* (2013.01); *A61H 3/00* (2013.01); *A61F 2005/0179* (2013.01); *A61H 2201/165* (2013.01)

(58) Field of Classification Search

CPC ................ A61H 3/00; A61H 2003/007; A61H 2003/002; A61H 1/0262; A61H 1/0292; A61F 5/02; A61F 5/026; A61F 5/028; A62B 9/04; A62B 18/02; A62B 18/00

See application file for complete search history.

(56) References Cited

U.S. PATENT DOCUMENTS 3,570,011 A * 3/1971 Naig ......................... A61F 5/02 2/44
4,049,164 A * 9/1977 Sullivan .................. B63C 11/22 224/633

(Continued)

FOREIGN PATENT DOCUMENTS

| | | | |
|---|---|---|---|
| CN | 218138043 | U | 12/2022 |
| EP | 3738464 | A1 | 11/2020 |
| GB | 2059750 | A | 4/1981 |

OTHER PUBLICATIONS

Jiazhen Chen. A.F.A.—"Powered Exoskeleton Suit for Firefighter" Product Design—Concept, 2014 Melbourne Design Awards Gold, A'Design Award Winner 2016 Silver.

*Primary Examiner* — Kari K Rodriquez
(74) *Attorney, Agent, or Firm* — McGlew and Tuttle, P.C.

(57) ABSTRACT

An exoskeleton (100) includes a flexible support component (5.*l*, 5.*r*, 2.*l*, 2.*r*, 4.*l*, 4.*r*) that a user (B) can attach to his/her body in order to lift a load. An object can be attached to a rigid back plate (1). The user (B) is a firefighter, for example, and the object on the back plate (1) is a compressed air cylinder (50) for breathing air. The flexible support component (5.*l*, 5.*r*, 2.*l*, 2.*r*, 4.*l*, 4.*r*) is in a mechanical operative connection with an energy storage device (10.*l*). The energy storage device (10.*l*) takes up kinetic energy when the user (B) bends his/her upper body forwards. The energy storage device (10.*l*) releases the taken-up kinetic energy again when the user (B) straightens up again. Preferably, the user (B) can interrupt and restore the mechanical operative connection by means of an actuating element.

20 Claims, 7 Drawing Sheets

(56) References Cited

U.S. PATENT DOCUMENTS

| | | | | |
|---|---|---|---|---|
| 5,954,250 | A * | 9/1999 | Hall | A62B 25/00 224/629 |
| D443,113 | S | 5/2001 | Chodorow | |
| 6,401,715 | B1 * | 6/2002 | Luthe | A62B 9/04 128/202.19 |
| 8,353,433 | B2 * | 1/2013 | Wrigley | A62B 25/00 224/633 |
| 2012/0184881 | A1 * | 7/2012 | Kobayashi | A61F 5/026 601/33 |
| 2017/0360588 | A1 | 12/2017 | Yangyuenthanasan et al. | |
| 2019/0151689 | A1 * | 5/2019 | Peng | A62B 25/00 |
| 2019/0231574 | A1 * | 8/2019 | Kazerooni | A61F 5/02 |
| 2023/0019536 | A1 | 1/2023 | Zanella et al. | |
| 2023/0087418 | A1 * | 3/2023 | Topa | A62B 35/0025 128/205.22 |
| 2023/0271034 | A1 * | 8/2023 | Muir | H01R 13/6205 128/205.22 |
| 2024/0408742 | A1 * | 12/2024 | Hatch | B25J 9/0006 |

* cited by examiner

EXOSKELETON WITH A BACK PLATE

CROSS REFERENCE TO RELATED APPLICATIONS

This application claims the benefit of priority under 35 U.S.C. § 119 of German Application 10 2023 107 409.1, filed Mar. 24, 2023, the entire contents of which are incorporated herein by reference.

TECHNICAL FIELD

The invention relates to an exoskeleton.

BACKGROUND

A user can attach such an exoskeleton to his/her body. The exoskeleton is able to support the user in standing up and lifting loads. The exoskeleton relieves the user's musculoskeletal system when standing up and lifting, especially when the user lifts an object and carries it while lifting.

SUMMARY

It is an object of the invention to provide an exoskeleton which supports a user better than known exoskeletons in lifting a load.

The problem is solved by an exoskeleton with features disclosed herein. Advantageous embodiments of the exoskeleton according to the invention are disclosed herein.

The terms "up" ("top", "above"), "down" (bottom"), "left", "right", "front", "back", "horizontal" and "vertical" used below refer to the usual orientations that occur when a user wears the exoskeleton according to the invention, and more specifically to the viewing direction of the user looking in the direction in which the tips of his/her feet are pointing.

The exoskeleton according to the invention comprises a flexible support component (flexible carrying component). This flexible support component can be attached to the body of a user and detached from the body again. Because the support component is flexible, it adapts to a certain degree to the geometry of the user's body.

Furthermore, the exoskeleton according to the invention comprises a rigid back plate (rigid back section/rigid back frame). An object to be carried can be attached, preferably detachably attached, to this rigid back plate. The back plate extends in one plane, is preferably at least 30 centimeters wide and is mechanically connected to the flexible support component or can at least temporarily be mechanically connected to it, preferably detachably connected. The back plate is configured in such a way that an object can be attached to the back plate. Thanks to the mechanical connection, the flexible support component holds the rigid back plate. This makes it easier for a user to carry an object that is attached to the back plate. With a detachable connection, the back plate can be detached from the flexible support component. This makes it easier to clean the flexible support component.

When a user wears the exoskeleton, the flexible support component is located between the user's body and the back plate.

The exoskeleton further comprises a rigid energy storage component. This energy storage component comprises an energy storage device (energy accumulator). The energy storage device may comprise at least two spatially spaced apart elements, for example, a left energy storage element disposed near the left leg of a user and a right energy storage element disposed near the right leg.

The energy storage device is able to take up and release again kinetic energy. When the user bends his/her upper body forwards, the energy storage device takes up kinetic energy. When the user straightens up again and moves his/her own weight and optionally the weight of an object they are carrying upwards, the energy storage device releases kinetic energy and thereby helps the user to straighten up again and optionally to lift the object.

Preferably, the energy storage device is a purely mechanical component, i.e. it does not consume any electricity and does not emit any electricity. As a result, the energy storage device does not need to meet any requirements that an electrical component that is worn by a user must meet. In many cases, an electrical component requires its own power supply unit, which takes up space and has a weight. In many cases the invention saves the need of providing such an electrical component.

On the one hand, the energy storage component is mechanically connected or connectable, preferably detachably connected, to the back plate. On the other hand, the energy storage component is mechanically connected or connectable, preferably detachably connected, to the flexible support component.

The exoskeleton can be attached to the user's body using the flexible support component. The flexible support component is attached to the user's body after the user has put on the exoskeleton. The energy storage device is a component of the rigid energy storage component. There is a mechanical operative connection between the flexible support component and the energy storage device. This mechanical operative connection is configured as follows: When a user has put on the exoskeleton and the user bends his/her upper body forwards, at least part of the support component follows this movement. Thanks to the mechanical operative connection, the energy storage device takes up kinetic energy when the user bends his/her upper body forwards and thereby moves at least part of the flexible support component relative to the energy storage device. The energy storage device releases at least part of the kinetic energy which was taken up when the user straightens up again. The kinetic energy released is transferred to the user's body with the aid of the mechanical operative connection and the support component. In this way, the energy storage device helps the user to stand up and lift his/her own weight and optionally a load, while the user straightens up again and the energy storage device releases kinetic energy.

At least one object can be attached to the back plate of the exoskeleton, preferably detachably. Thanks to the back plate, the user has his/her hands free and the object on the back plate does not hinder the user in his/her work. Because the back plate is rigid, it is robust compared to a possible other embodiment.

The exoskeleton according to the invention thus combines two effects: On the one hand, it makes it easier for a user to carry at least one object, whereby this object is attached to the back plate and the user has his/her hands free. Secondly, the exoskeleton makes it easier for a user to lift the object attached to the back plate, optionally together with objects on or at the user's body, for example protective clothing or tools. The user's musculoskeletal system is relieved compared to an embodiment without energy storage.

The back plate is rigid and extends in one plane. As a result, in many cases the back plate prevents, to a greater extent than a flexible back plate or a rod-shaped element, an object attached to the back plate or rod-shaped element from performing movements relative to the back plate and thus relative to a user's body. Such relative movements are often undesirable. Thanks to the back plate, it is also possible in many cases to attach several objects with different dimensions to the same back plate at the same time or at least one after the other. This would not be the case if an object were to be attached to a rod-shaped element.

According to the invention, the flexible support component is located between the body of a user and the back plate. The back plate, in turn, is located between the flexible support component and an object that is attached to the back plate. Thanks to this feature, there is a distance between the back plate and the object on the one hand and the flexible support component and the user's body on the other. As a result, a user's mobility is less restricted than if the object were attached directly to a carrying component that rests against a user's body.

The invention makes it possible to manufacture the flexible support component from at least one suitable flexible material and the back plate from at least one suitable rigid material. The material used in each case can be adapted to the intended use of the flexible support component or the rigid back plate.

In one embodiment, the energy storage component has a curved shape, particularly preferably the shape of a bow or U. When the exoskeleton is placed on the user's body, a segment of the energy storage component is connected to the back plate. Two legs of the energy storage component point forwards or vertically or diagonally downwards. The segment is located between the legs. The user's body is located between these two legs. In many cases, two lever arms occur with this configuration. A movement of the user and thus the flexible support component over a relatively long distance causes a movable component of the energy storage device, for example a spring, to be moved over a relatively short distance. This means that the user only needs to exert relatively little force to bend the upper body forwards. On the other hand, the energy storage device can be configured to be relatively space-saving.

The energy storage device is preferably configured as a mechanical energy storage device and particularly preferably comprises at least one mechanical or pneumatic spring, optionally two parallel springs. This configuration makes it possible to realize the energy storage device as a purely mechanical component or as an arrangement with several purely mechanical components. Preferably, the energy storage device is arranged inside the rigid energy storage component and is thus protected to a certain extent against damage and environmental influences from the outside.

According to the invention, the flexible support component contacts the user's body when the user has put on the exoskeleton. In one embodiment, the support component comprises a shoulder part and a hip-leg part. When the exoskeleton is placed on the user's body, the shoulder part rests against the user's shoulders or surrounds the user's shoulders. In one embodiment, the hip-leg part or at least one component of the hip-leg part rests against the user's hips. In another implementation, the hip-leg part or at least two components of the hip-leg part rest against both legs of the user. A combination of these two implementations is possible: one component rests on the hips, two further components on the two legs.

The embodiment with the shoulder portion and the hip-leg portion often results in the weight of an object connected to the back plate being distributed over several parts of the user's body and/or the or each energy storage device taking up a relatively large amount of kinetic energy in an operationally safe manner when the user bends his/her upper body forward.

In a further embodiment of this configuration, the hip-leg part comprises two leg parts that can be fitted around the two legs of a user, namely a left leg part for the left leg and a right leg part for the right leg. A left connecting element mechanically connects the left leg part to the energy storage component, while a right connecting element mechanically connects the right leg part to the energy storage component. Preferably, both connecting elements are rigid. These two mechanical connections are implemented by means of the two connecting elements and two joints. Thanks to these two joints, each leg part can be rotated relative to the energy storage component either forwards or backwards about a common axis of rotation of the leg part. "Common" means that both leg parts can be rotated about the same leg part axis of rotation. The leg part rotation axis is preferably horizontal. The left leg part can be rotated forwards or backwards independently of the right leg part and vice versa. This embodiment makes it possible to connect the flexible support component to the user's legs without significantly hindering the user when walking, kneeling or bending down.

In one embodiment of this further implementation, these two mechanical joints not only allow each leg part to be rotatable forwards or backwards relative to the energy storage component, but also to be rotatable either outwards or inwards, also independently of the other leg part. It is possible that the two joints just mentioned are double joints.

It is also possible that the exoskeleton comprises two additional joints instead of two double joints, which allow the leg parts to rotate inwards and outwards. In one embodiment, each connecting element comprises two components, whereby the two components are rotatably connected to each other by an additional joint. Each additional joint realizes an additional axis of rotation, namely a left additional axis of rotation and a right additional axis of rotation. Particularly preferably, these two additional axes of rotation are parallel to one another and are perpendicular to the common leg part axis of rotation, this common leg part axis of rotation enabling the two leg parts to move forwards and backwards relative to the energy storage component as just described.

According to the invention, the energy storage component takes up kinetic energy when the user bends forward and releases kinetic energy when the user straightens up again. The flexible support component is mechanically connected to the energy storage component. Preferably, this mechanical connection comprises two joints. Thanks to these two joints, the flexible support component can be rotated relative to the energy storage component about an axis of rotation either forwards or backwards. Thanks to this configuration, the rigid energy storage component restricts the user relatively little when the user walks or otherwise moves. This axis of rotation can be the common leg part axis of rotation just described.

According to the invention, the back plate is mechanically connected to the energy storage component. In a preferred embodiment, the back plate can be rotated relative to the energy storage component about a back plate axis of rotation, optionally to the left or to the right, i.e. in two opposite directions of rotation. The back plate axis of rotation is preferably a horizontal axis of rotation and is preferably perpendicular to the common leg part axis of rotation just described. This configuration also helps to ensure that the user's movements are relatively unrestricted by the exoskeleton.

According to the invention, the rigid back plate is mechanically connected to the flexible support component. In one embodiment, the back plate comprises an upper part and a lower part. The upper part can be moved linearly relative to the lower part in two opposite directions. In particular, when the user has put on the exoskeleton, the upper part can be moved upwards or downwards relative to the lower part. The upper part is connected to a shoulder part of the flexible support component. This shoulder part can be placed on the user's shoulders. The lower part is mechanically connected to the rigid energy storage component. The configuration with the two parts of the back plate makes it easier to adapt the exoskeleton to the height of a user and/or to a vertical dimension of an object to be connected to the back plate. The shoulder part is preferably only connected to the energy storage component via the back plate, and the vertical extension of the back plate can be changed. This makes it easier to adapt the flexible support component to the dimensions of a user's body.

According to the invention, the flexible support component is in a mechanical operative connection with the energy storage device. In one embodiment, a user who has put on the exoskeleton can optionally interrupt and re-establish this mechanical operative connection without having to take off the exoskeleton and without requiring the assistance of another person to do so. In many cases, the user can bend the upper body upwards with less effort when the mechanical operative connection is interrupted than when the mechanical operative connection is established. When the mechanical operative connection is interrupted, the energy storage device naturally does not take up any kinetic energy. According to this embodiment, an actuating element is attached to the flexible support component, preferably to a shoulder part of the flexible support component, optionally to a hip-leg part. The user who has put on the exoskeleton can actuate this actuating element from the outside, preferably with one hand and preferably even if the user is wearing gloves. The actuating element is in an operative connection with the energy storage device. Actuating the actuating element causes the mechanical operative connection to be either established or interrupted. It is possible that there are two actuating elements, for example one on the shoulder plate and one on the hip/leg part.

This configuration increases flexibility and wearing comfort when using the exoskeleton. A user can choose to use the exoskeleton with activated or deactivated energy storage device. "Deactivated energy storage device" means that the mechanical operative connection between the flexible support component and the energy storage is interrupted. For example, a user deactivates the energy storage device if no object at all or only a light object is attached to the back plate and/or activates the energy storage device if at least one heavy object or several objects that are heavy in total are attached to the back plate.

In one embodiment, the energy storage component comprises at least one actuator. The actuator is capable of establishing or interrupting or optionally establishing or interrupting the mechanical operative connection just described. The actuating element is in an operative connection with this actuator. The actuator is only required to change the state of the mechanical operative connection, but not to maintain the mechanical operative connection or to store and release kinetic energy.

Preferably, the actuator comprises an electrical component and the operative connection is an electrical operative connection. The actuator and actuator element may also comprise a mechanical arrangement. In one embodiment, a restoring element, for example a spring, is used to establish the mechanical operative connection. The actuator can be activated, and the activated actuator acts to interrupt the mechanical operative connection against the force of the reset element. The reverse principle is also possible.

The invention also relates to an arrangement comprising an exoskeleton according to the invention. This arrangement further comprises a container, a face mask and a fluid connection between the container and the face mask. The container is capable of holding breathing air, preferably compressed air. The container is attached to the outside of the back plate, preferably detachably attached. The face mask can be placed on the user's head. Thanks to the fluid connection, the user can breathe in air from the container. The exoskeleton makes it easier for the user wearing the container to stand up. For example, the user is a firefighter, and the exoskeleton according to the invention or the arrangement just described are part of that firefighter's protective equipment.

The invention is described below by means of embodiment examples. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
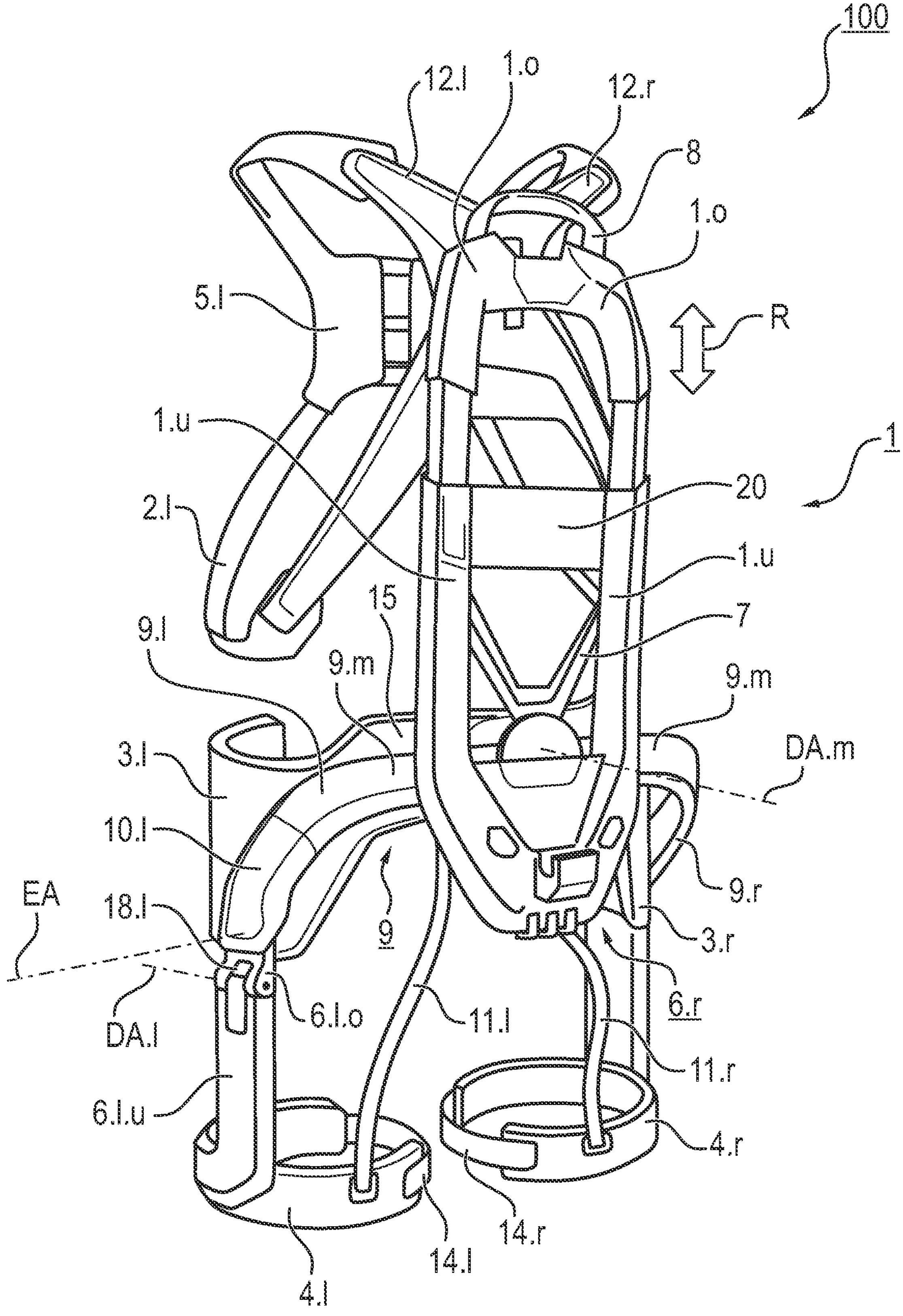
FIG. 1 is a perspective view showing the exoskeleton of the embodiment example from a viewing direction in which the back plate points towards the viewer.

Referring to the drawings, in an embodiment example, the exoskeleton according to the invention is used by a firefighter or other rescue worker. The term "user" of the exoskeleton is used below. The user attaches a flexible support component described below to his/her body. This flexible support component carries a back plate. At least one component of the user's personal protective equipment is attached to the back plate, in particular a compressed air cylinder for a compressed air breathing apparatus 50.

In one application, the exoskeleton according to the invention is configured to be used by a firefighter. In the embodiment example, all components of the exoskeleton fulfill the requirements that are placed on the protective equipment of a firefighter, in particular requirements with regard to flammability, heat, decontamination and mechanical stress.

The exoskeleton 100 of the embodiment example comprises a back plate 1. The back plate 1 comprises a rigid upper part 1.*o* and a rigid lower part 1.*u*. The upper part 1.*o* has the shape of an inverted U, the lower part 1.*u* has the shape of a U. An optional stiffener 7 reinforces the lower part 1.*u*. The rigid back plate is preferably made of steel or another suitable metal or metallic alloy.

Figure 2:
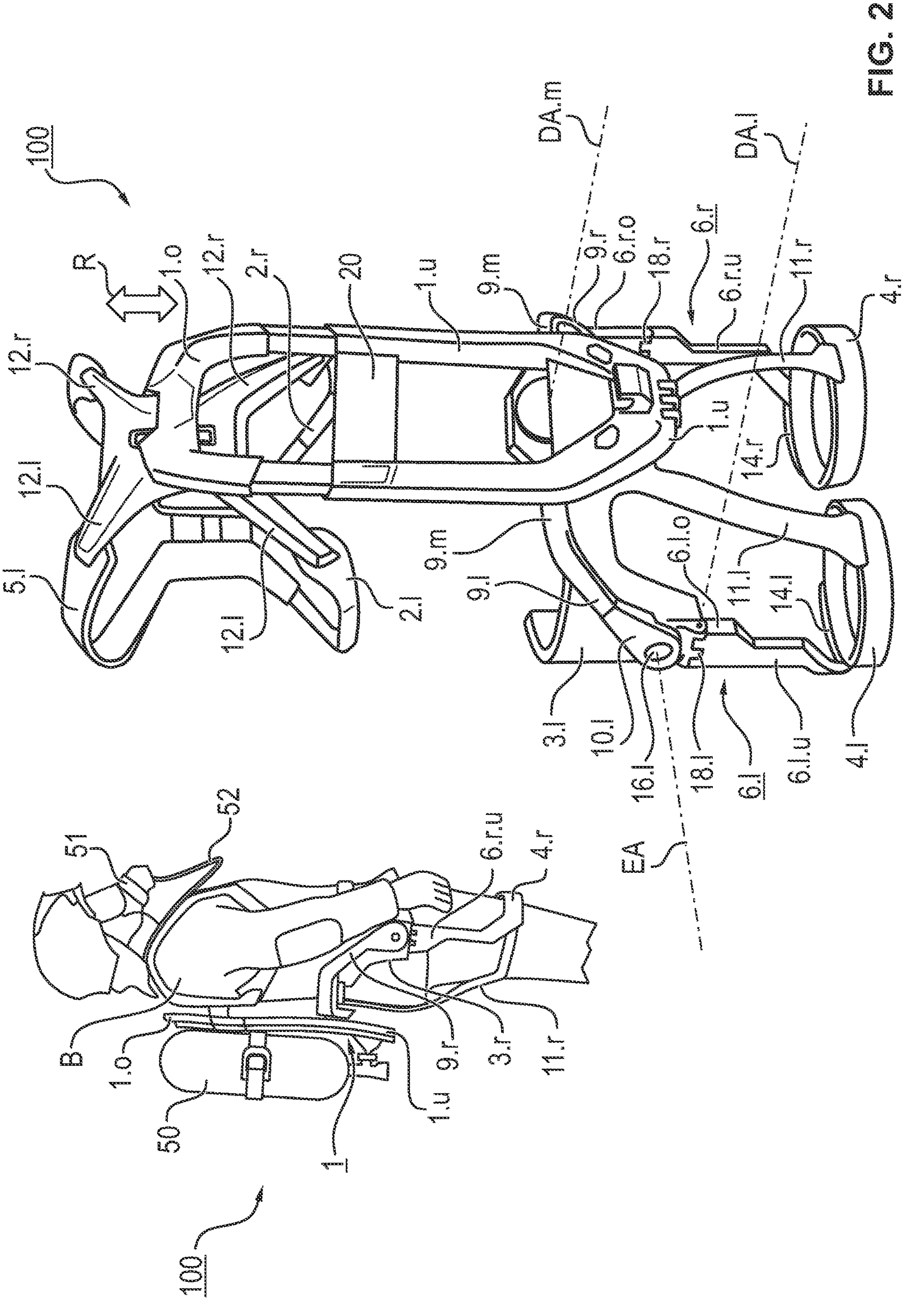
FIG. 2 is perspective views of the exoskeleton of FIG. 1 and a user with the exoskeleton of FIG. 1.
Figure 3:
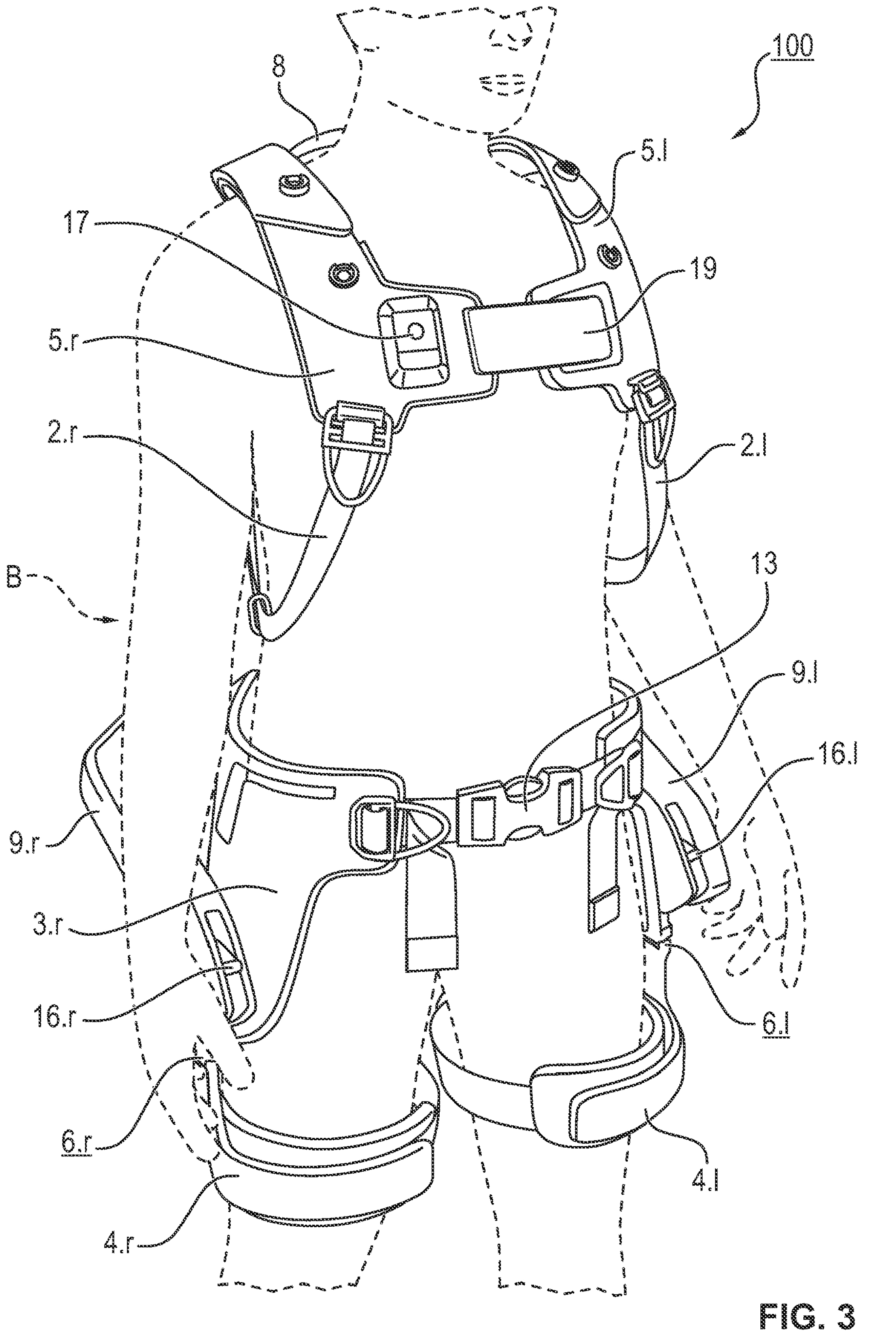
FIG. 3 is a perspective view showing a user in dashed line with the exoskeleton of FIG. 1 or FIG. 2, with the back plate located behind the user.
Figure 4:
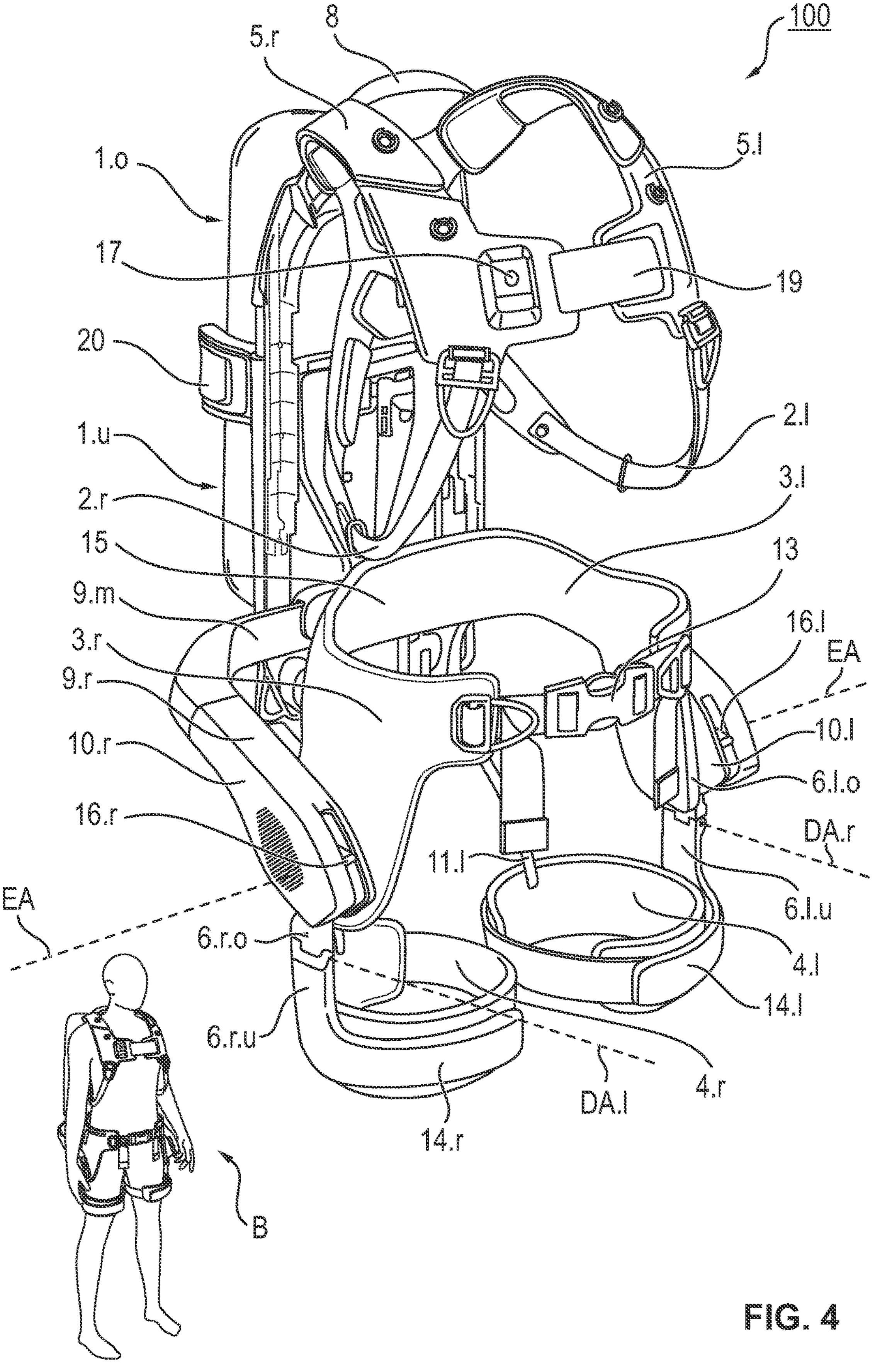
FIG. 4 is perspective views of the exoskeleton of FIG. 1 or FIG. 2 from the viewing direction of FIG. 3 and a user with this exoskeleton.

FIG. 1 and FIG. 2 show the exoskeleton 100 of the embodiment example, with the back plate 1 pointing towards the viewer. FIG. 3 and FIG. 4 show the exoskeleton 100 of FIG. 1, with the back plate 1 facing away from the viewer. FIG. 2 and FIG. 3 show the exoskeleton 100 and a user B wearing the exoskeleton 100. In FIG. 4, user B is shown at the bottom left wearing the exoskeleton 100.

FIG. 2 shows a user B on the left, in this case a firefighter wearing the exoskeleton 100. User B is wearing a face mask 51 and a protective helmet with a Holland cloth. A compressed air cylinder 50 for breathing air is detachably attached to the back plate 1. A fluid guide unit in the form of a hose 52 connects the compressed air bottle 50 to the face mask 51.

The vertical dimensions of the two-part back plate 1 can be changed. This feature makes it easier to adapt the exoskeleton 100 to the height of the user B and/or to the height of a compressed air cylinder 50. Different users can wear the same exoskeleton 100 in succession and adjust the vertical dimensions of the back plate 1 as required. One implementation of the two-part back plate 1 is described below.

The two parts 1.*o* and 1.*u* are connected to each other in the shape of a telescopic head. In the embodiment shown, the lower part 1.*u* or at least one upper segment of the two legs of the lower part 1.*u* has the shape of a tube or two tubes in each case. The two legs of the upper part 1.*o* are pushed into the two legs of the lower part 1.*u* from above. Thanks to the telescopic connection, the upper part 1.*o* can be moved linearly upwards and downwards relative to the lower part 1.*u*, which is indicated by a double arrow R in FIG. 1. Preferably, a latching connection or snap connection locks the upper part 1.*o* in a desired position relative to the lower part 1.*u*. Thanks to the overlap between the two parts 1.*o* and 1.*u*, the telescopic connection results in a mechanically stable back plate 1.

The following components of the exoskeleton 100 are attached to the upper part 1.*o:*

- a left shoulder strap 5.*l* and a right shoulder strap 5.*r*, which are located on the left and right shoulders of user B respectively,
- a flexible and stretchable connecting strap 19, which detachably connects the two shoulder straps 5.*l* and 5.*r* in front of the chest of the user B,
- a strap 2.*l* for the left shoulder strap 5.*l* and a strap 2.*r* for the right shoulder strap 5.*r*, which are located under the left and right shoulders of user B respectively,
- a belt spider 12.*l* for the left shoulder strap 5.*l* and a belt spider 12.*r* for the right shoulder strap 5.*r*, which connect the left shoulder strap 5.*l* and the right shoulder strap 5.*r* respectively to the upper part 1.*o* of the back plate 1, and
- one carrying handle 8 on the upper part 1.*o*.

Preferably, the components 5.*l*, 5.*r*, 2.*l*, 2.*r*, 12.*l*, 12.*r*, 19 are flexible and bendable in order to be able to adapt to the body shape of a user B of the exoskeleton. These components 5.*l*, 5.*r*, 2.*l*, 2.*r*, 12.*l*, 12.*r*, 19 are part of the flexible support of the embodiment example.

A rigid hip support (strap) 9 is attached to the lower part 1.*u*. This hip support 9 acts as the energy storage component and, in the embodiment example, has approximately the shape of a stirrup, particularly preferably the shape of a forward-pointing U. A middle segment 9.*m* of the hip support 9 is connected to the lower part 1.*u* of the back plate 1, preferably detachably connected. In the embodiment example, this middle segment 9.*m* is connected to the lower part 1.*u* as follows: The back plate 1 can rotate relative to the hip support 9 in two opposite directions of rotation about a horizontal axis of rotation DA.m to the left and to the right. The middle segment 9.*m* is located between a left hip support leg (left hip support segment) 9.*l* and a right hip support leg (right hip support segment) 9.*r* of the hip support 9. The two legs 9.*l* and 9.*r* point obliquely forwards and downwards. When the user B has put on the exoskeleton 100, his/her body is located at the level of his/her hips between the two hip support legs 9.*l*, 9.*r*, 9.*r*, and the middle segment 9.*m* is located behind his/her kidney. Preferably, a pad on the middle segment 9.*m* points towards the body of the user B. Preferably, the two hip support legs 9.*l*, 9.*r* and the middle segment 9.*m* are rigidly connected to each other and form a single rigid component.

A two-part left thigh stirrup 6.*l* is attached to the free end of the left hip support leg 9.*l*, a two-part right thigh stirrup 6.*r* is attached to the free end of the right hip support leg 9.*r*. The left thigh stirrup 6.*l* comprises an upper part 6.*l*.*o* and a lower part 6.*l*.u, the right thigh stirrup 6.*r* also comprises an upper part 6.*r*.*o* and a lower part 6.*r*.u.

A left hip pad (hip part) 3.*l* is attached near the free end of the left hip support leg 9.*l*, and a right hip pad (hip part) 3.*r* is attached near the free end of the right hip support leg 9.*r*. The two flexible hip pads 3.*l* and 3.*r* are connected to each other by a kidney pad 15. In one possible state of the exoskeleton 100, the kidney pad 15 is located between the body of the user B and the lower part 1.*u* of the back plate 1. In addition, the user B can detachably connect the two hip pads 3.*l* and 3.*r* to each other by means of a fastener 13 in front of his/her abdomen. The pads 3.*l*, 3.*r*, 15 and the fastener 13 form a single flexible component which surrounds the body of the user B and are also part of the flexible support component of the embodiment example. At least the two hip pads 3.*l*, 3.*r*, optionally also the kidney pad 15, can be elastically compressed and can therefore adapt even better to a changing body geometry of the user B.

A U-shaped free end of the left hip support leg 9.*l* surrounds a flattened segment of the left upper part 6.*l*.o, a U-shaped free end of the right hip support leg 9.*r* surrounds a flattened segment of the right upper part 6.*r*.o, see FIG. 2.

A left swivel joint 16.*l* rotatably connects the following three components of the exoskeleton 100:

- the left hip support leg 9.*l*,
- the upper left part 6.*l*.*o* and
- the left hip pad 3.*l*.

Accordingly, a right swivel joint 16.*r* rotatably connects the following three components of the exoskeleton 100:

- the right hip support leg 9.*r*,
- the upper right part 6.*r*.*o* and the right hip pad 3.*r*.

The two swivel joints 16.*l* and 16.*r* realize a common horizontal leg part axis of rotation EA. Both the two thigh stirrups 6.*l* and 6.*r* as well as the flexible component with the two hip pads 3.*l* and 3.*r* and the kidney pad 15 can move forwards and backwards relative to the hip support 9 and also relative to each other about this common leg part axis of rotation EA, independently of each other. This allows the user B, who has put on the exoskeleton 100, to walk relatively unhindered on the one hand and to bend his/her upper body forwards on the other hand.

The lower left part 6.*l*.u is rotatably mounted relative to the upper left part 6.*l*.*o* by a left swivel joint 18.*l*, namely about a horizontal axis of rotation DA.l, which is perpendicular to the leg part axis of rotation EA. This allows the lower left part 6.*l*.u to rotate outwards and inwards relative to the upper left part 6.*l*.o. Correspondingly, the right lower part 6.*r*.u is rotatably mounted relative to the right upper part 6.*r*.*o* about a horizontal axis of rotation DA.r, namely by a right swivel joint 18.*r*.

User B can place a left leg pad (leg part) 4.*l* around his/her left leg and a right leg pad (leg part) 4.*r* around his/her right leg. The two leg pads 4.*l*, 4.*r* are also flexible. The left leg pad 4.*l* is attached to the lower left part 6.*l*.u of the left thigh stirrup 6.*l*, the right leg pad 4.*r* is attached to the lower right part 6.*r*.u of the right thigh stirrup 6.*r*. A flexible left leg strap 11.*l* connects the left leg pad 4.*l* to the left hip pad 3.*l*, a flexible right leg strap 11.*r* connects the right leg pad 4.*r* to the right hip pad 3.*r*. The two leg pads 4.*l*, 4.*r* and the two leg straps 11.*l*, 11.*r* are also part of the flexible support component of the embodiment example.

One consequence of the swivel joints 16.*l*, 16.*r*, 18.*l*, 18.*r* is the following: When the user B has put on the exoskeleton 100, the hip support 9 and thus also the back plate 1 can be rotated forwards and backwards relative to the hip pads 3.*l*, 3.*r* and the leg pads 4.*l*, 4.*r*. This configuration makes it easier for user B in particular to put the carrier component on his/her body and take it off again later.

A mechanical energy storage device is arranged inside the hip support 9. In one embodiment, a left actuator 10.*l* is located inside the left hip support leg 9.*l*, and a right actuator 10.*r* is located inside the right hip support leg 9.*r*. In another embodiment, an actuator 10 is located inside the middle segment 9.*m*. These two embodiments can be combined. These two implementations can be combined with each other. The actuators 10 or 10.*l*, 10.*r* together form the energy storage device of the embodiment example or belong to the energy storage device. Each actuator 10, 10.*l*, 10.*r* comprises, for example, a torque spring or a linear spring.

Figure 6:
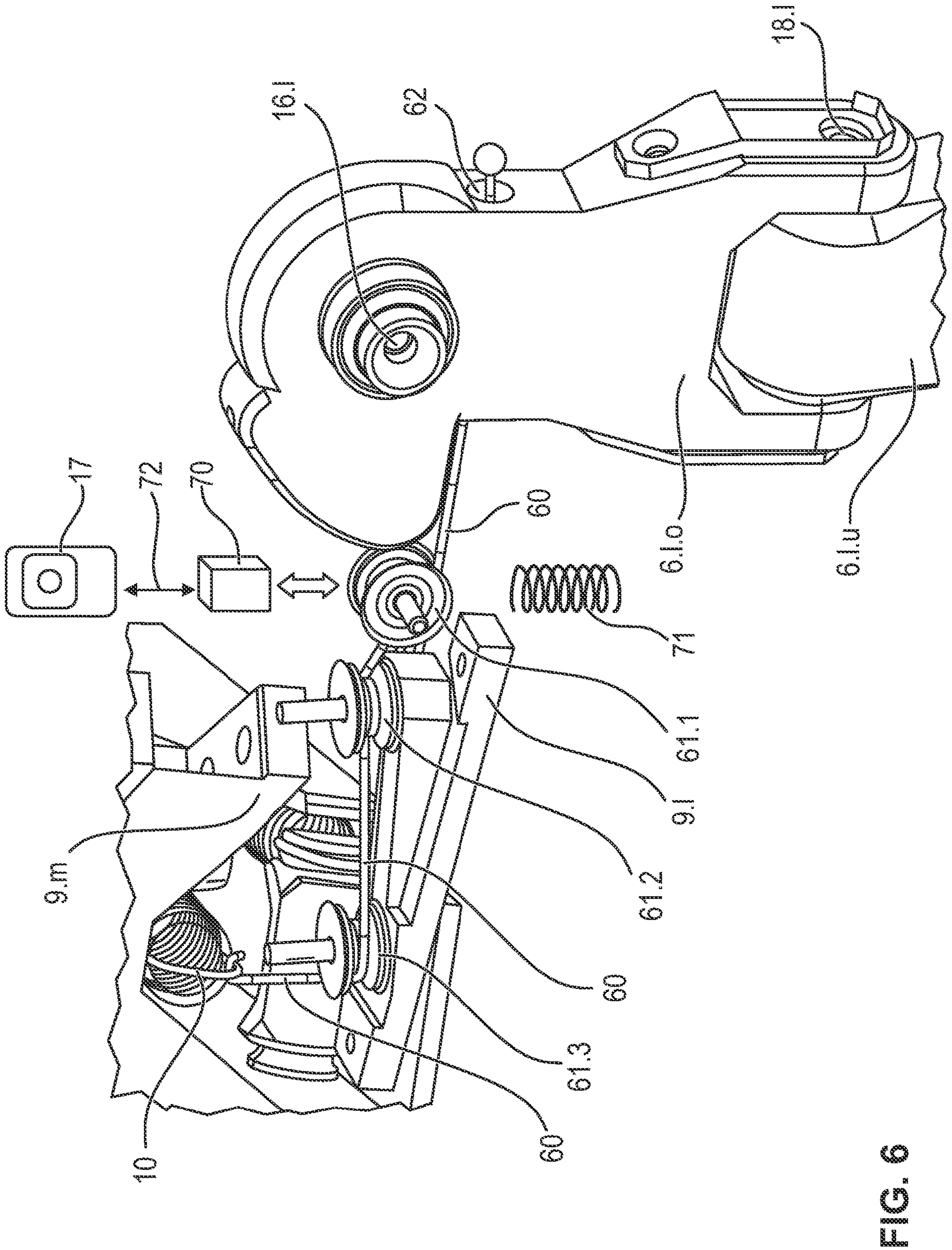
FIG. 6 is a perspective view of an exemplary implementation for the mechanical operative connection between the energy storage device and the support component and schematically showing the electrical operative connection between the actuating element and the mechanical operative connection.

According to the invention, a mechanical operative connection connects the flexible support component to the energy storage device. FIG. 6 shows an exemplary implementation of this mechanical operative connection. In this example, an energy storage device 10 in the form of a spring is arranged inside the middle segment 9.*m*. When the user B bends forward, this spring 10 is pulled apart and thus takes up kinetic energy. The spring 10 contracts again and releases at least part of the taken-up kinetic energy when the user B straightens up. The longitudinal axis of the spring 10 runs parallel to the axis of rotation of the leg part EA. The same applies if two parallel springs 10.*l*, 10.*r* are used instead of a single spring 10.

FIG. 6 shows a detail of this mechanical operative connection. A cable or flexible wire 60 connects the left end of the spring 10 to the upper part 6.*l*.*o* of the left thigh support 6.*l*. The cable 60 is guided around three deflection pulleys 61.1, 61.2, 61.3 and through a hole 62 in the upper part 6.*l*.o. The deflection pulleys 61.1, 61.2, 61.3 are located inside the left hip support leg 9.*l*. The wall of the left hip support leg 9.*l* is omitted in FIG. 6.

In a preferred embodiment, the user B can interrupt this mechanical operative connection and re-establish it later. When the mechanical operative connection is interrupted, the user B needs to exert less work to bend forward because the energy storage device 10, 10.*l*, 10.*r* then does not take up any kinetic energy. On the other hand, the energy storage device 10, 10.*l*, 10.*r* does not release any kinetic energy when user B straightens up again.

Figure 5:
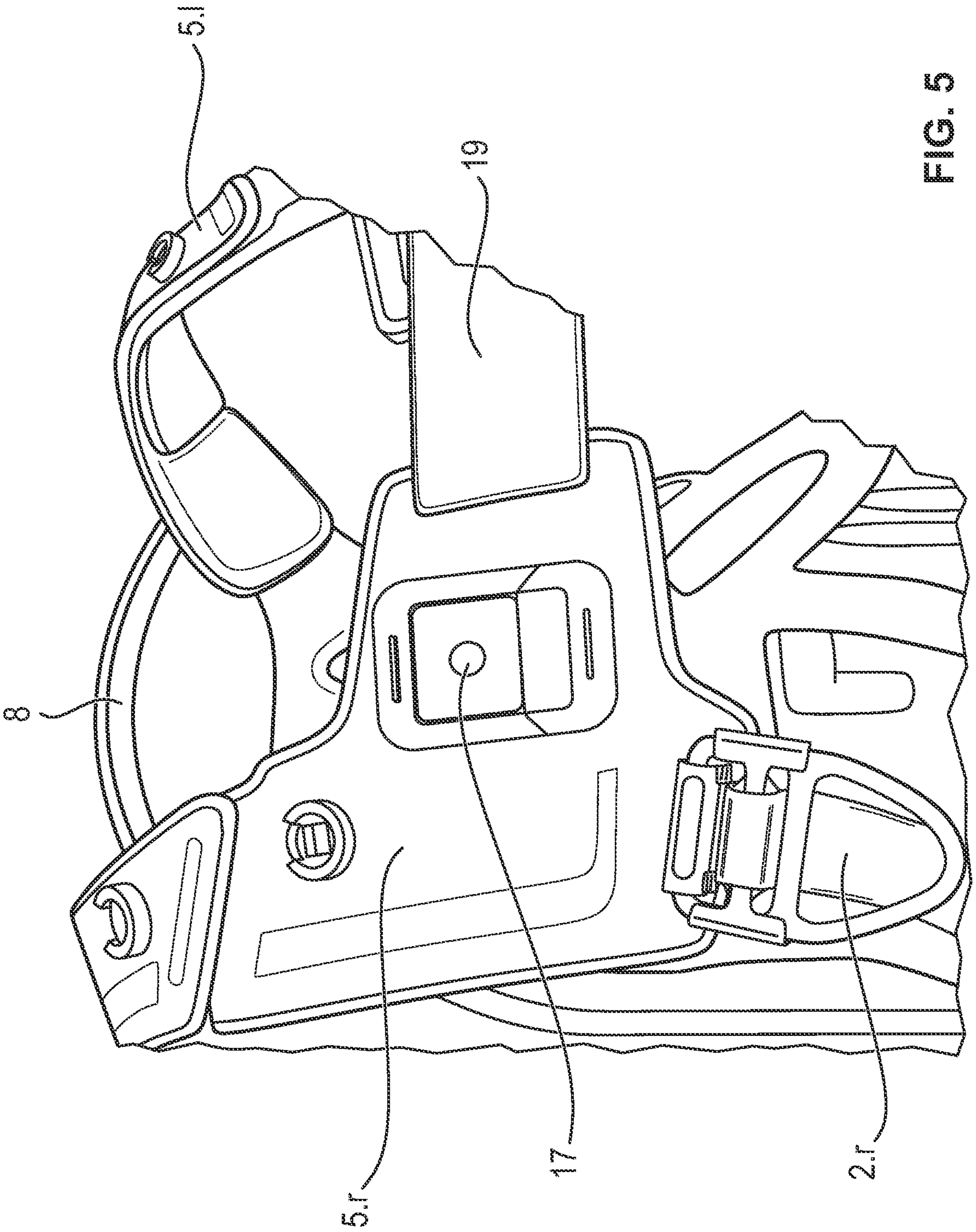
FIG. 5 is a perspective view of an actuating element on the right shoulder strap.

An actuating element 17 is attached to a shoulder strap 5.*l* or 5.*r*. This actuating element 17 can be actuated from the outside and comprises, for example, a switch and/or a button. Because the actuating element 17 is attached to a shoulder strap 5.*l* or 5.*r*, in many cases the user B can actuate this actuating element 17 relatively comfortably with one hand, even if the user is wearing a glove. FIG. 5 shows an example of an actuating element 17 on the right shoulder strap 5.*r*. It is also possible that an actuating element is attached to each shoulder strap 5.*l* and 5.*r*.

The user B can interrupt the operative connection between the flexible support component and the energy storage device 10, 10.*l*, 10.*r* and restore the operative connection later by actuating the actuating element or one actuating element 17 for both interrupting and restoring.

The actuating element 17 is in an operative connection with the mechanical operative connection just described with reference to FIG. 6, or with another mechanical operative connection. FIG. 6 shows an example of an electrical operative connection 72 with an electrical actuator 70 and a mechanical reset element in the form of a spring 71. In the implementation form shown, the spring 71 acts to pull the deflection pulley 61.1 downwards and thereby tighten the cable 60. The tightened cable 60 establishes the mechanical operative connection. The actuator 70 is in a schematically shown electrical operative connection 72 with the actuating element 17 and acts to pull the deflection pulley 61.1 upwards against the force of the spring 71. By actuating the actuating element 17, the user B switches the actuator 70 on and off again. As long as the deflection pulley 61.1 is pulled sufficiently far upwards, the cable 60 is no longer taut and the mechanical operative connection is interrupted.

Inside the hip support 9 there is a power supply unit for the actuator 70, which is not shown. The actuator 70 and the power supply unit are only required to interrupt or restore the mechanical operative connection, i.e. only for a state transfer, but not for taking up or releasing kinetic energy.

Other forms of realization are also possible, as the actuating element 17 is able to interrupt and re-establish the mechanical operative connection.

Figure 8:
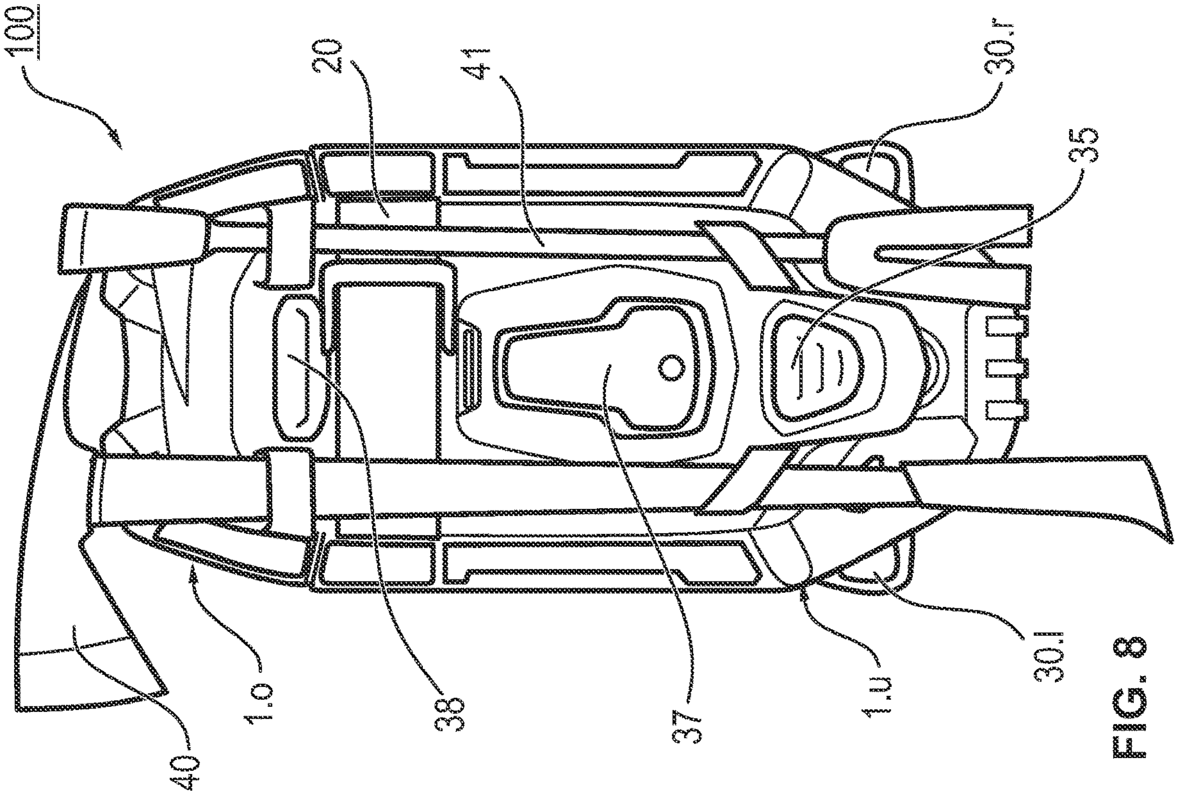
FIG. 8 is a perspective view showing the back plate of FIG. 7 with objects and indicator lights.
Figure 7:
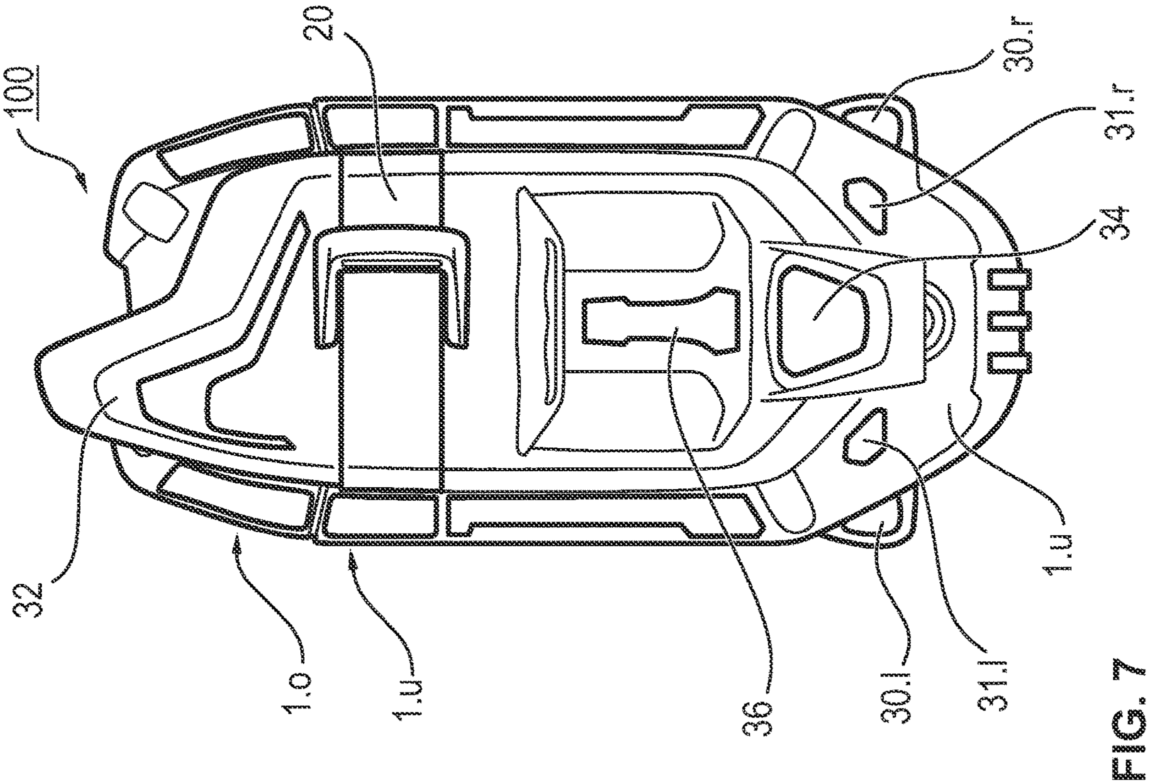
FIG. 7 is a rear view showing the back plate without objects and without indicator lights on the back plate.

FIG. 7 and FIG. 8 show an example of the back plate 1 viewed from behind. The upper part 1.*o* is pushed as far as possible into the lower part 1.*u*, so that the back plate 1 has the smallest possible vertical dimensions. The user B, not shown here, is located behind the back plate 1 in this viewing direction. A flexible and stretchable retaining strap 20 is guided and tensioned around the lower part 1.*u* of the back plate 1, which is able to press an object against the lower part 1.*u*.

With the aid of two eyelets 30.*l* and 30.*r* and two recesses 31.*l*, 31.*r*, the lower part 1.*u* of the back plate 1 can be detachably connected to the hip support 9.

In the embodiment example, an antenna 32 of a communication unit is shown in the upper part 1.*o* of the back plate 1. With the aid of this communication unit, user B can exchange messages wirelessly with other firefighters.

A reflector 33 and a smaller indicator light 38 ("buddy light L") are embedded in the upper part 1.*o*. A recess 34 for a larger indicator light ("buddy light XL") 35 and a recess 36 for a component 37 comprising a power supply unit and a further reflector are recessed into the lower part 1.*u*.

Various devices can be detachably attached to the back plate 1 using the stretchable retaining strap 20. An axe 40 and a breaking tool 41 are shown as examples in FIG. 8.

While specific embodiments of the invention have been shown and described in detail to illustrate the application of the principles of the invention, it will be understood that the invention may be embodied otherwise without departing from such principles.

LIST OF REFERENCE CHARACTERS

| | |
|---|---|
| 1 | Back plate, includes the two parts 1.o, 1.u |
| 1.o | Upper part of the back plate 1, has the shape of an inverted U, telescopically connected to the lower part 1.u |
| 1.u | Lower part of the back plate 1, has the shape of a U, telescopically connected to the upper part 1.o |
| 2.l | Strap for the left shoulder strap 5.l |
| 2.r | Strap for the right shoulder strap 5.r |
| 3.l | Left hip pad (hip part) |
| 3.r | Right hip pad (hip part) |
| 4.l | Left leg pad (leg part), connected to the left leg strap 11.l |
| 4.r | Right leg pad (leg part), connected to the right leg strap 11.r |
| 5.l | Left shoulder strap, connected to the belt tensioner 12.l |
| 5.r | Right shoulder strap, connected to the belt tensioner 12.r |
| 6.l | Left thigh stirrup, connected to the hip support 9 and the left hip pad 3.l via the joint 16.l |
| 6.r | Right thigh stirrup, connected to the hip support 9 and the right hip pad 3.r via the joint 16.r |
| 7 | Stiffener for the lower part 1.u of the back plate 1 |
| 8 | Carrying handle, attached to the upper part 1.o of the back plate 1 |
| 9 | Rigid hip support, comprises the two legs 9.l, 9.r and a middle segment, accommodates the actuators 10, 10.l, 10.r, acts as an energy storage component |
| 9.l | Left leg of the hip support 9, accommodates the actuator 10.l |
| 9.m | Middle segment of the hip support 9, arranged between the two hip support legs 9.l and 9.r, accommodates the actuator 10 |
| 9.r | Right leg of the hip support 9, accommodates the actuator 10.r |
| 10 | Actuators 10 forms the energy storage device or belongs to the energy storage device. Each actuator 10, 10.l, 10.r comprises, for example, a torque spring or a linear spring. |
| 10.l | Left actuator together with the right actuator 10.r form the energy storage device of the embodiment example or belong to the energy storage device, arranged in the left leg 9.l |
| 10.r | Right actuator together with the left actuator 10.l form the energy storage device or belong to the energy storage device, arranged in the right leg 9.r |
| 11.l | Left leg strap, connects the left leg pad 4.l with the hip support 9 |
| 11.r | Right leg strap, connects the right leg pad 4.r with the hip support 9 |
| 12.l | Belt tensioner for the left shoulder strap 5.l |
| 12.r | Belt tensioner for the right shoulder strap 5.r |
| 13 | Closure for hip pads 3.l, 3.r |
| 14.l | Strap for right leg pad 4.l |
| 14.r | Strap for left leg pad 4.r |
| 15 | Kidney pad between the two hip pads 3.l and 3.r |
| 16.l | Joint between the left hip support leg 9.l, the left thigh support 6.l and the left hip pad 3.l, allows rotation about the leg part axis of rotation EA |
| 16.r | Joint between the right hip support leg 9.r, the right thigh support 6.r and the right hip pad 3.r, allows rotation about the leg part axis of rotation EA |
| 17 | Actuating element for the actuators 10.l and 10.r, attached to a shoulder strap 5.l or 5.r, is in one form of realization in an electrical operative connection 72 with the actuator 70 |
| 18.l | Joint between the upper part 6.l.o and the lower part 6.l.u of the left thigh stirrup 6.l, allows rotation about the axis of rotation DA.l |

-continued

| | |
|---|---|
| 18.r | Joint between the upper part 6.r.o and the lower part 6.r.u of the right thigh stirrup 6.r, allows rotation about the axis of rotation DA.r |
| 19 | Flexible connecting strap between the two shoulder straps 5.l and 5.r |
| 20 | Flexible retaining strap on the lower part 1.u of the back plate 1 |
| 30.l, 30.r | Eyelets on the lower part 1.u |
| 31.l, 31.r | Recesses in the lower part 1.u |
| 32 | Antenna, integrated in the upper part 1.o |
| 33 | Reflector on upper part 1.o |
| 34 | Recess in the lower part 1.u for the indicator light 35 |
| 35 | Larger indicator light, detachably inserted in recess 34 |
| 36 | Recess in the lower part 1.u for component 37 |
| 37 | Component with a power supply unit and a further reflector, inserted into recess 36 |
| 38 | Smaller indicator light, attached to the upper part 1.o |
| 40 | Axe detachably attached to the back plate 1 using the retaining strap 20 |
| 41 | Breaking tool, detachably attached to the back plate 1 using the retaining strap 20 |
| 50 | Compressed air cylinder for breathing air, detachably attached to the back plate 1, is in a fluid connection with the face mask 51 via the hose 52 |
| 51 | Face mask, is in a fluid connection with the compressed air cylinder via hose 52 |
| 52 | Hose between the face mask 51 and the compressed air cylinder 50 |
| 60 | Wire or cable connecting the left thigh stirrup 6.l to the left hip support leg 9.l |
| 61.l, 61.2, 61.3 | Pulleys around which the wire or cable 60 is guided |
| 62 | Hole in the upper part 6.1.o, through which the cable 60 is guided |
| 70 | Actuator for the deflection pulley 61.l, connected to the actuating element 17 via the electrical operative connection 72 |
| 71 | Return element in the form of a spring for the deflection pulley 61.l |
| 72 | Electrical operative connection between the actuating element 17 and the actuator 70 |
| 100 | Exoskeleton |
| B | User wearing the exoskeleton 100 |
| DA.l | Horizontal axis of rotation, about which the upper part 6.l.o of the left thigh stirrup 6.l can be rotated outwards and inwards relative to the lower part 6.l.u, is implemented by the left joint 18.l |
| DA.m | Horizontal axis of rotation about which the back plate 1 can be rotated relative to the hip support 9 |
| DA.r | Horizontal axis of rotation, about which the upper part 6.r.o of the right thigh stirrup 6.r can be rotated outwards and inwards relative to the lower part 6.r.u, is implemented by the right joint 18.r |
| EA | Horizontal leg part axis of rotation about which the flexible support component can be rotated forwards and backwards relative to the rigid hip support 9, at the same time axis of rotation about which the two thigh supports 6.l, 6.r can be rotated forwards and backwards relative to the rigid hip support 9, implemented by the joints 16.l, 16.r |
| R | Opposite directions in which the upper part 1.o can be moved linearly up and down relative to the lower part 1.u |

What is claimed is:

1. An exoskeleton comprising:

a flexible support component that can be placed on the body of a user;

a rigid back plate configured such that an object can be attached to the back plate; and a rigid energy storage component with an energy storage device, wherein the back plate is connected to the flexible support component, wherein the flexible support component is placed between and configured for operative connection between a body of a user and the back plate, wherein the rigid energy storage component is mechanically connected both to the back plate and to the flexible support component, and wherein the flexible support component is in a mechanical operative connection with the energy storage device such that the energy storage device, with the flexible support component in operative connection with the body of the user, takes up kinetic energy upon the user bending the user's upper body forward and releases at least part of the kinetic energy having taken up upon the user straightening up the user's upper body.

2. The exoskeleton according to claim 1, wherein the flexible support component comprises:

a shoulder part; and a hip-leg part, wherein the shoulder part is configured to be placed on shoulders of the user, wherein the hip-leg part is configured to be placed on hips of a user and/or around legs of the user, wherein the shoulder part is mechanically connected to the back plate, and wherein the hip-leg part is mechanically connected to the energy storage component.

3. The exoskeleton according to claim 2, wherein the hip-leg part comprises two leg parts and the exoskeleton comprises two rigid connecting elements, wherein the two leg parts can be placed around the two legs of the user, wherein each connecting element mechanically connects a respective leg part to the energy storage component, and wherein these mechanical connections are implemented by means of two joints such that each leg part is rotatable forwards and backwards relative to the energy storage component about a common leg part axis of rotation.

4. The exoskeleton according to claim 3, wherein the mechanical connection between the leg parts and the energy storage component is implemented with two additional joints, wherein each leg part is additionally rotatable outwards and inwards relative to the energy storage component about a respective further axis of rotation, and wherein each further axis of rotation is perpendicular to the common leg part axis of rotation.

5. The exoskeleton according to claim 1, wherein the mechanical connection between the energy storage component and the flexible support component comprises two joints such that the flexible support component is rotatable forwards and backwards relative to the energy storage component about an axis of rotation, wherein a relative forward rotation of the flexible support component causes the energy storage device to take up kinetic energy via the mechanical operative connection, and wherein a relative backward rotation of the flexible support component causes the energy storage device to release kinetic energy via the mechanical operative connection.

6. The exoskeleton according to claim 1, wherein the back plate is rotatable relative to the energy storage component about a back plate axis of rotation in two opposite rotational directions.

7. The exoskeleton according to claim 1, wherein the back plate comprises an upper part and a lower part, wherein the flexible support component comprises a shoulder part, wherein the shoulder part is configured to be placed on shoulders of the user, wherein the upper part of the back plate is mechanically connected to the shoulder part, wherein the lower part of the back plate is mechanically connected to the rigid energy storage component, and wherein the upper part is linearly shiftable relative to the lower part in two opposite directions.

8. The exoskeleton according to claim 7, wherein the upper part has a U shape with two upper part legs, wherein the lower part has a U shape with two lower part legs, wherein the two upper part legs engage the two lower part legs, or the two lower part legs engage the two upper part legs.

9. The exoskeleton according to claim 1, further comprising an actuating element connected to the flexible support component, the actuating element being operatively connected to the energy storage device such that an actuation of the actuating element selectively establishes or interrupts the mechanical operative connection between the flexible support component and the energy storage device.

10. The exoskeleton according to claim 9, wherein the energy storage component comprises at least one actuator, wherein the actuator is configured to establish and/or interrupt the mechanical operative connection between the flexible support component and the energy storage device, and wherein the actuating element is in an operative connection with the actuator.

11. The arrangement comprising an exoskeleton according to claim 1, and further comprising:

a container configured to hold and deliver breathing air, the container being attached to the back plate;

a face mask configured to be applied to a head of the user; and a fluid connection between the container and the face mask.

12. A process comprising:

providing an exoskeleton, the exoskeleton comprising:

a flexible support component that can be placed on the body of a user;

a rigid back plate configured such that an object can be attached to the back plate; and a rigid energy storage component with an energy storage device, wherein the back plate is connected to the flexible support component, wherein the flexible support component is placed between and configured for operative connection between a body of a user and the back plate, wherein the rigid energy storage component is mechanically connected both to the back plate and to the flexible support component, and wherein the flexible support component is in a mechanical operative connection with the energy storage device such that the energy storage device, with the flexible support component in operative connection with the body of the user, takes up kinetic energy upon the user bending the user's upper body forward and releases at least part of the kinetic energy taken up upon the user straightening up the user's upper body; and deploying the exoskeleton as part of a firefighter's protective equipment.

13. An exoskeleton comprising:

a flexible support component that can be placed on the body of a user;

an object to be attached and carried;

a rigid back plate configured to support the object with the object attached to the back plate and carried by the back plate, the back plate extending in a plane; and a rigid energy storage component with an energy storage device, wherein the flexible support component is placed between and configured for operative connection between a body of a user and the back plate and comprises: a shoulder part which is configured to be placed on shoulders of the user; and a hip-leg part, which is configured to be placed on hips of a user and/or around legs of the user, wherein the shoulder part is mechanically connected to the back plate, wherein the hip-leg part is mechanically connected to the energy storage component, wherein the back plate is rotatable relative to the energy storage component about a back plate axis of rotation in two opposite rotational directions and the rigid energy storage component is mechanically connected both to the back plate and to the hip-leg part of the flexible support component, with the back plate located between the hip-leg part of the flexible support component and the object that is attached to the back plate and carried by the back plate, and wherein the hip-leg part is in a mechanical operative connection with the energy storage device such that the energy storage device, with the hip-leg part in operative connection with the body of the user, takes up kinetic energy upon the user bending the user's upper body and the rigid back plate rotating forward about the back plate axis of rotation and releases at least part of the kinetic energy, that was taken up, upon the user straightening up the user's upper body and the rigid back plate rotating backward about the back plate axis of rotation.

14. The exoskeleton according to claim 13, wherein the hip-leg part comprises two leg parts and the exoskeleton further comprises two rigid connecting elements, wherein the two leg parts are configured to be placed around the two legs of the user, wherein each of the rigid connecting elements mechanically connects a respective leg part to the energy storage component, and wherein these mechanical connections are implemented by means of two joints such that each leg part is rotatable forwards and backwards relative to the energy storage component about a common leg part axis of rotation.

15. The exoskeleton according to claim 14, wherein the mechanical connection between the leg parts and the energy storage component is implemented with two additional joints, wherein each leg part is additionally rotatable outwards and inwards relative to the energy storage component about a respective further axis of rotation, and wherein each further axis of rotation is perpendicular to the common leg part axis of rotation.

16. The exoskeleton according to claim 13, wherein the mechanical connection between the energy storage component and the hip-leg part comprises two joints such that the hip-leg part is rotatable forwards and backwards relative to the energy storage component about an axis of rotation, wherein a relative forward rotation of the hip-leg part causes the energy storage device to take up kinetic energy via the mechanical operative connection, and wherein a relative backward rotation of the hip-leg part causes the energy storage device to release kinetic energy via the mechanical operative connection.

17. The exoskeleton according to claim 13, wherein the back plate comprises an upper part and a lower part, wherein the upper part of the back plate is mechanically connected to the shoulder part, wherein the lower part of the back plate is mechanically connected to the rigid energy storage component, and wherein the upper part is linearly shiftable relative to the lower part in two opposite directions.

18. The exoskeleton according to claim 13, further comprising an actuating element connected to the hip-leg part, the actuating element being operatively connected to the energy storage device such that an actuation of the actuating element selectively establishes or interrupts the mechanical operative connection between the hip-leg part and the energy storage device.

19. The exoskeleton according to claim 18, wherein the energy storage component comprises at least one actuator, wherein the actuator is configured to establish and/or interrupt the mechanical operative connection between the hip-leg part and the energy storage device, and wherein the actuating element is in an operative connection with the actuator.

20. The exoskeleton according to claim 13, wherein the object comprises a container configured to hold and deliver breathing air, the container being attached to the back plate and carried by the back plate.

* * * * *